United States Patent
Gouin et al.

[11] Patent Number: 5,955,068
[45] Date of Patent: Sep. 21, 1999

[54] BIODEGRADABLE POLANHYDRIDES DERIVED FROM DIMERS OF BILE ACIDS, AND USE THEREOF AS CONTROLLED DRUG RELEASE SYSTEMS

[75] Inventors: Sebastien Gouin, Montréal; Xiao-Xia Zhu, Dollard-des-Ormeaux, both of Canada

[73] Assignee: Universite de Montreal, Montreal, Canada

[21] Appl. No.: 08/951,423

[22] Filed: Oct. 16, 1997

[30] Foreign Application Priority Data

Apr. 14, 1997 [CA] Canada ................................ 2202676

[51] Int. Cl.[6] .............................. A61K 31/74; A61F 2/02
[52] U.S. Cl. ....................................... 424/78.17; 424/426
[58] Field of Search ................................ 424/78.17, 426

[56] References Cited

PUBLICATIONS

Goiuin et al, New biodegradable polymers synthesized from the bile acids, Polymer Preparation, 38(2), 586–587, 1997.

*Primary Examiner*—Carlos Azpuru
*Attorney, Agent, or Firm*—Bacon & Thomas

[57] ABSTRACT

New biodegradable polyanhydrides are disclosed, which are prepared by homopolymerization of dimer of bile acid, especially lithocholic acid, or bycopolymerization with linear dicarboxylic acid, especially sebacic acid. These biodegradable polyanhydrides have degradation kinetics and a release rate that make them particularly useful for controlled drug release. More specifically, the degradation kinetics of such anhydrides and the release rate of molecules embedded therein make them useful as matrices for controlled drug release systems. The rates of degradation and release can be adjusted by the copolymer composition. The near zero-order kinetics of release of the drug embedded in the matrices made of such anhydrides, make the same particularly useful since they can deliver an active ingredient at a constant rate for long period of time, avoiding the inauspicious saw-tooth pattern of conventional systemic administration.

18 Claims, 4 Drawing Sheets

BIODEGRADABLE POLANHYDRIDES DERIVED FROM DIMERS OF BILE ACIDS, AND USE THEREOF AS CONTROLLED DRUG RELEASE SYSTEMS

FIELD OF THE INVENTION

The present invention relates to new biodegradable polyanhydrides prepared from dimers of bile acids.

It also relates to the use of such new biodegradable polyanhydrides as matrices for the manufacture of controlled drug release systems.

BRIEF DESCRIPTION OF THE PRIOR ART

Bioerodible polymers have been used for various applications in biomedical and pharmaceutical fields, including tissue replacements and controlled release system of bioactive compounds.

The use of biodegradable polymer drug carriers has significant advantages over the conventional systemic administration of medicine. The conventional drug carriers produce a peak in the plasma drug level as the drug enters the body, followed by a rapid decrease as the drug is metabolized, thus requiring repeated drug administrations. The biodegradable polymer drug carriers permit a controlled release of an active principle over a long period of time, i.e., months or even years. These systems can maintain a constant level of drugs in the plasma in a specified therapeutic range. Thus, the unwanted side-effects of high plasma drug level and the non-therapeutic low plasma drug level of the conventional administration sawtooth pattern can be avoided. Furthermore, the polymer drug carriers prevent the patient from being exposed to a massive excess of drugs over the quantities required. They also help to localize the release of the drug at the desired site of action.

Hydrogels can be used as drug carriers for controlled delivery systems and have been extensively investigated for this purpose. Degradable systems offer a significant advantage over the non-erodible systems, since the degradation products will eventually be absorbed or metabolized, thus avoiding the necessity to surgically remove the implant.

Bioerodible polymer delivery systems are attractive also in terms of predictability of release, if the release is controlled only by the degradation process. In many cases, however, once the diffusion of the active principle through polymer matrix takes place, the release process becomes difficult to control. Diffusion of the active principle occurs as the matrix starts to erode in a homogenous manner. This leads to a progressive loosening of the matrix which change its permeability and then diffusion of the active principle becomes increasingly faster. Many factors may affect the erosion rate: bond lability, hydrophobicity, cristallinity, dissolution of degradation products and porosity. To achieve a surface erosion of zero-order kinetics, the ideal polymer should have a hydrophobic backbone to prevent bulk erosion and diffusion, and very labile bonds to insure that the hydrolytic degradation is much faster than the penetration of water into the matrix.

Many types of polymers have been studied for their degradation properties, such as polyesters, polyamides, polyurethanes, polyphospazenes, but only polyorthoesters and polyanhydrides have been designed to achieve a zero-order degradation rate. Because of the backbone stability of polyorthoesters, excipients must be added in the matrix to promote degradation. These excipients, usually inorganic water-soluble salts, tend to swell in aqueous media and thus promote diffusional release. In contrast, polyanhydrides may be sufficiently labile in hydrolysis to produce heterogeneous erosion, without the addition of any excipient.

Polyanhydrides were first synthesized by Hill and Carothers in the 1930s as a substitute of polyester in the textile industry (see Hill J. et all, J. Am Chem. Soc. 1930, 52, 4110 and 1932, 54, 1569). However, they were discarded because of their hydrolytic instability. It is known that the erosion rate of polyanhydrides can be changed several thousand folds only by changing the monomers or the composition of the copolymers. It is also known that there are many ways to polymerize a diacid into polyanhydride. The use of dehydrative coupling agents, such as phenyl N-phenylphosphoro-amidochloridate or bis[2-oxo-3-axazolidinyl]phosphinic chloride, yields only impure oligomers, since the salt formed cannot be removed. Phosgene or the less toxic diphosgene can be used to prepare polyanhydrides of the reagents restricts their uses. However, high molecular weight polyanhydrides can be obtained via melt polycondensation of mixed anhydride prepolymers at high temperatures.

SUMMARY OF THE INVENTION

An object of the present invention is to provide new biodegradable polyanhydrides derived from dimers of bile acids.

Bile acids are natural, amphiphilic compounds stored in the gallbladder, which serve as emulsifiers for the solubilization of fats and lipids in food. Examples of such acids are;

lithocholic acid;

cholic acid;

desoxycholic acid;

ursodesoxycholic acid;

etc. . .

In accordance with the present invention, it has been found that when such biocompounds are used in the preparation of polymer materials, the so-prepared materials, are better tolerated in the biological environment, especially in the gastrointestinal tract. It has also been found that such materials are biodegradable and have controlled degradation properties that make them useful as matrices for the controlled release of drug.

The biodegradable polyanhydrides according to the invention are prepared by homopolymerization of bile acid dimers of the general formula I:

$$A—B—A \qquad (I)$$

wherein A is a bile acid radical and B is a linear dicarboxylic acid "spacer" of the formula II:

$$HOOC—(CH_2)_n—COOH \qquad (II)$$

wherein n is an integer that ranges from 1 to 12 and is preferably equal to 6 or 8.

The biodegradable polyanhydrides according to the invention can also be prepared by copolymerisation of dimers of the general formula I as defined hereinabove, with linear dicarboxylic acids of the general formula II as also defined hereinabove.

These biodegradable polyanhydrides have degradation kinetics and a release rate that make them particularly useful for controlled drug release. More specifically, the degradation kinetics of such anhydrides and the release rate of molecules embedded therein make them useful as matrices for controlled drug release systems. The rates of degradation and release can be adjusted by the copolymer composition. The near zero-order kinetics of release of the drug embedded in the matrices made of such anhydrides make the same particularly useful since they can deliver an active ingredient at a constant rate for long period of time, avoiding the inauspicious saw-tooth pattern of conventional systemic administration.

Thus, another object of the invention is the use of the above biodegradable anhydrides for the manufacture of controlled drug release matrices.

The following detailed description deals exclusively with the synthesis and properties of biodegradable polyanhydrides derived from a dimer of lithocholic acid, which is one of the bile acids. However, the invention is not restricted to the use of this dimer (nor to the use of sebacic acid). As a matter of fact, it applies to all the compounds encompassed by the above formulae I and II.

DETAILED DESCRIPTION OF THE INVENTION

EXPERIMENTAL

Materials and Instruments

Acetic anhydride was purchased from Aldrich and used as received. The probe, p-nitroaniline, was purchased from Kodak and used as received. The solvents were also purchased from Aldrich. Chloroform and petroleum ether were dried over molecular sieves 4A (Aldrich) and redistilled. THF was refluxed with sodium and redistilled.

Infrared spectra were recorded on an ATI Mattson Genesis FT-IR spectrophotometer with KBr pellets. Nuclear magnetic resonance (NMR) spectra were recorded at 23° C. on a Brucker AMX-300 spectrometer operating at 300.1 MHz for 1H in deuterated chloroform which also served as an internal reference (7.27 ppm for $^1$H). The chemical shifts are given in ppm and coupling constants (J) in Hz. The molecular weight of the polymers soluble in THF were determined by size exclusion chromatography (SEC) at 33° C. using a 5 wt % solution in THF on a Waters 410 system (Waters) using polystyrene as the standard. The glass transition temperatures of the polymers were determined on a differential scanning calorimeter (DSC 2910) from TA Instrument with a heating rate of 20° C./min. in the range of –100 to 300° C. The concentration of the probe molecule in the degradation buffer was determined by U.V. absorbance on a Varian DMS 100 UV-Visible spectrophotometer at 455 nm.

Preparation of the Polymers

A prepolymer of sebacic acid (PreSA) was prepared as described by Conix (A. Macro Synth., 1966, 2, 95). A lithocholic acid dimer was also prepared as described by the present inventors (Steroids, 1996, 61, 664). These starting materials were used for the preparation of polyanhydrides according to the invention, following the reactions shown schematically in FIG. 1.

Prepolymer

A solution of 1 g of the lithocholic acid dimer prepared by the inventors, viz. bis(5(-cholan-24-oic-3(-yl) sebacate, in 6 ml of acetic anhydride was heated to 120° C. in an oil bath for 1 h. The solvent was partially removed and the mixed anhydride prepolymer was allowed to crystallize at –10° C. The product was filtered out, washed with a small amount of cold acetic anhydride and dried under vacuum at room temperature for two days. The requested bis (5(-cholan-24-oic acid 3(-yl) sebacate prepolymer (PreLCA) was obtained with a yield of 50%.

Its IR and $^1$H NMR spectrum characteristics are as follows:

IR: 2927 and 2865 (C—H), 1820 (C=O, anhydride) 1730 (C=O, ester);

$^1$H NMR (selected signals): 4.72 (2H, m, C3-CH), 2.23 (4H, t, CH2 of sebacate), 2.15 (6H, s, acetic CH3), 1.32 (4H, CH2 of sebacate), 0.96 (6H, d, J=6, C21 CH3), 0.91 (6H, s, C19 CH3), 0.71 (6H, s, C18 CH3).

Homopolymer

The preparation of polyanhydride homopolymers was achieved by melt polycondensation of PreLCA under an inert gas. The prepolymer (PreLCA) was placed in a polymerization tube equipped with a capillary inlet tube for gas and a side-arm for the vacuum. The prepolymer was then heated in an oil bath to 140° C. under a flow of nitrogen. After the prepolymer was melted, the polymerization was allowed to proceed in vacuo for 72 h. The polymer was then purified by reprecipitation from petroleum ether to produce the requested bis (5(-cholan-24-oic acid 3(-yl) sebacate poly(anhydride) (PLCA).

The IR and $^1$H NMR spectrum characteristics of this polymer are as follows:

IR: 2920 and 2870 (C—H), 1820 (C=O, anhydride) 1735 (C=O, ester);

$^1$H NMR (selected signals): 4.70 (2H, m, C3 H), 2.20 (4H, t, $CH_2$ of sebacate), 1.32 (4H, $CH_2$ of sebacate), 0.98 (6H, s, C21 $CH_3$), 0.90 (6H, s, C19 $CH_3$), 0.73 (6H, s, C18 $CH_3$).

Copolymers

PreLCA and PreSA were mixed together in a polymerization tube in various desired weight fractions, (50:50, 20:80 and 10:90). Polyanhydride copolymers P(LCA-co-SA) were thus prepared in the same manner as for the homopolymer.

Degradation and Release Kinetics

Matrices were prepared by mixing PLCA or P(LCA-co-SA) with p-nitroaniline and then pressing the mixture between two aluminum pellets at room temperature with a force of 8 metric tons/$m^2$. The matrices were cylindrical with a height of approximatly 1 mm. The total surface area of the matrices were 1.32 $cm^2$ and the sample weighed from 120 to 150 mg.

In vitro drug release studies were performed by placing the PLCA or P(LCA-co-SA) matrices in glass scintillation vials containing 10 ml of phosphate buffer (pH 7.4) at room temperature. The buffer was periodically changed, before 33% of the saturation concentration for a perfect sink effect in order to simulate the constant flow of biological liquid in the body, by removing the matrix from the vials and placing it in a vial containing fresh buffer. The absorbance of the collected buffer solution was measured at a wavelength of 455 nm. The concentration was determined from a standard curve constructed by measuring the absorption at 455 nm of pure p-nitroaniline at concentration from 0.01 to 0.4 mg/ml. In vitro erosion was studied by weighing the matrix periodically after drying at 60° C. for 24 h under vacuum.

RESULTS AND DISCUSSION

Generalities

Two methods can be used to polymerize the diacids used as starting naturals into polyanhydrides: dehydrative coupling and melt polycondensation.

The first method yields oligomers. The purification of the product is difficult as decomposition of the anhydrides occurs.

Figure 1:
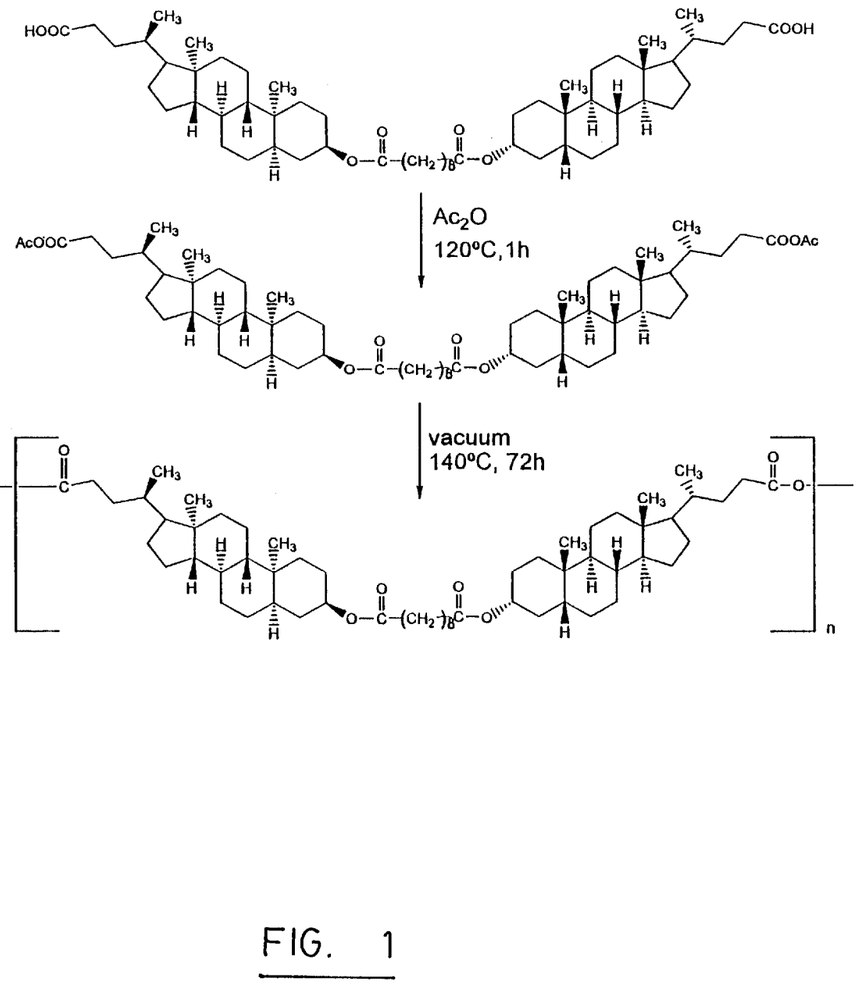
FIG. 1 is a schematic representation of the reactions that are carried out for the synthesis of a polyanhydride from dimers of lithocholic acid.

The second method shown in FIG. 1 involves the preparation of a prepolymer and the melt polycondensation of the prepolymer. This method requires very pure starting products to obtain the polymer. However, it does not requires strict stoichiometry as in other forms of polycondensation, since it is a self-polycondensation reaction.

As aforesaid the method used in the synthesis of prepolymers from lithocholic acid dimers and sebacic acid was adaptated from the procedure developed by Conix for the polycondensation of diacids. Long crystallization time was needed for a high yield and an acceptable purity. In the case of the lithocholic acid dimer prepolymer, it has been found that one week is necessary for a yield of 50% and that longer crystallization time improves the yield only slightly. The complete conversion of the acid group into anhydride is crucial to obtain the polymer. If some acid group remains, water will be produced during the melt polycondensation and only oligomers will be formed. It is difficult to verify the complete conversion of the acid group by proton NMR technique since the methyl proton peak of the acetic anhydride group (2.15 ppm) is overlapped with the proton signals of the steroid skeleton. FT-IR spectrophotometry is more useful to determine the completion of the reaction. The O—H absorption band at 3500 cm-1 disappears when the conversion of the acid group is complete.

Molecular Weights

The molecular weights of all the polymers synthesized were evaluated by several methods for comparison. First, NMR spectroscopy was used to evaluate the degree of polymerization (DP) of the homopolymer by calculating the integral ratio of methyl anhydride end group and C-21 methyl group of the steroid skeleton. Usually the 1H integral of methyl anhydride group can be identified when the DP is less than ten. A DP of at least ten was found, since no signal at 2.15 ppm can be detected and attributed to methly anhydride group. An average molecular weight of at least 10,000 g/mol was therefore suggested. Light scattering was also used to evaluate the Mn of the homopolymer. Solution of 5 wt % polymer in spectrograde THF was used for light scattering analysis. An average value of 12,000 g/mole was found. Size exclusion chromatography (SEC) of all the polymers have aslo been carried out using polystyrene as the standard. This technique gave a relative molecular weight since no suitable standards were available. Correction of the calibration curved obtained with polystyrene was made by using lithocholic acid dimer, which has a known molecular weight. Molecular weight of the polymer was then evaluated by assuming a perfect sigmo dal calibration curve profile, and Mn was found to be 18,000 g/mol with a polydispersity of 5.

As a result of these measurements, it appears that the polyanhydrides according to the invention have an average molecular weights in the range of 12,000 g/mol to 18,000 g/mol.

Transition Temperatures

The transition temperatures of homopolymer and copolymers prepared as disclosed hereinabove are shown in the following Table 1.

TABLE 1

Transition temperature of homo- and copolymer

| Polymer | Transition temperature | | |
|---|---|---|---|
| | $T_g$ (° C.) | $T_m$ (° C.) | $T_c$ (° C.) |
| PLCA | 85 | >250 | |
| P(LCA-SA)(50:50) | 30 | 63 | 42 |
| P(LCA-SA)(20:80) | 15 | 70 | 59 |
| P(LCA-SA)(10:90) | 13 | 77 | 71 |

*For the copolymers, the ratios indicated are weight percentage.

These transition temperatures were determined by DSC. Previous thermal history of the samples was erased by a preliminary heating cycle, from −100 to 250° C. at 20° C./min. The transition temperatures were then determined by heating the sample at 20° C./min from −100 to 300° C. for the homopolymer and from −100 to 250° C. for the copolymer, since the sebacic acid copolymers were prone to thermic degradation.

Figure 2:
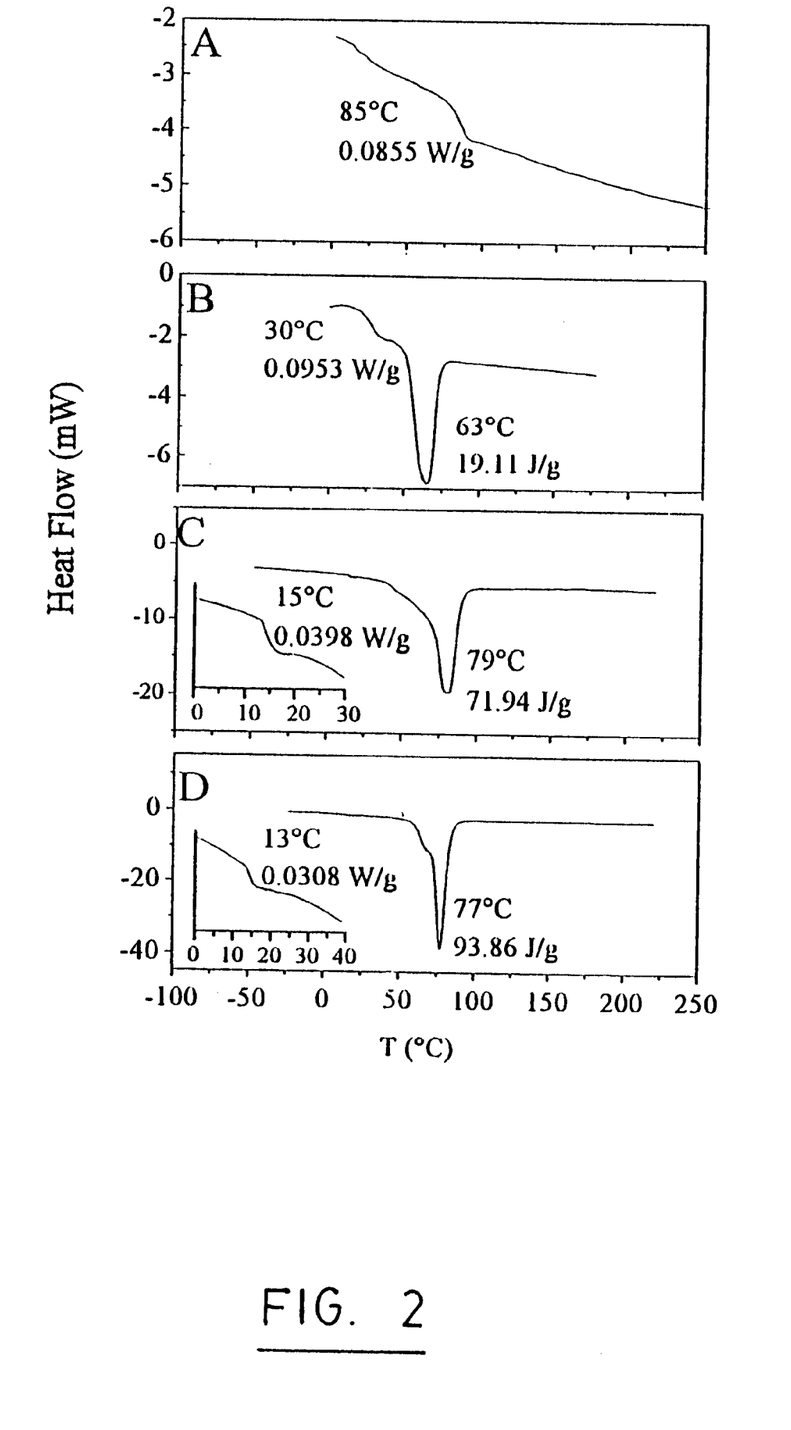
FIG. 2 are thermograms of the following homo- and copolymers: (A) PLCA; (B) P(LCA-co-SA) 50:50; (C) P(LCA-co-SA) 20:80; and (D) P(LCA-co-SA) 10:90.

The glass transition temperatures ($T_g$) of the polymers were found to depend on the chemical composition of the copolymers. Since sebacic acid is more flexible than lithocholic acid dimer, the higher composition of sebacic acid in the copolymer leads to lower $T_g$'s. When the weight proportion of sebacic acid in the different polymers increased from 0 to 80 wt %, the $T_g$ dropped from 85 to 4° C. Another factor that affects the $T_g$ is the molecular weight. Since sebacic acid polymerizes more easily than the lithocholic acid dimer, the more sebacic acid there is in the polymer, the higher the molecular weight, and therefore the higher the $T_g$. The thermograms where obtained and are reported in FIG. 2, show a strong melting peak for all the copolymers, indicating that the copolymers are quite crystalline. The homopolymer of lithocholic acid dimer does not show a melting peak and the degradation temperature is over 300° C. Obviously, the chains of this polymer are not very flexible, thus very difficult to cristallize.

Preparation of Matrices

Several processing methods have been tried to prepare the matrices for use in the degradation and release kinetic studies.

First, matrices were prepared by solvent evaporation from a solution of polymer and selected probe in chloroform. The solution was transferred into a Teflon mold and was allowed to evaporate very slowly at room temperature. Then the matrices are dried in vacuo at 60° C. The matrices formed, however, were so porous that they were not acceptable for the degradation and release kinetics studies. Even if chloroform was changed for THF (with a higher boiling point), the matrices remained too porous and fragile.

Processing of the polymer in nanoparticules was also considered. Two methods are available: emulsion in a mixed aqueous solvent and solvent evaporation. The first method is not acceptable for biodegradable polymers since water can degrade the polymer. The second method requires large amounts of the product not yet available.

Therefore, compression molding appears to be best suited for the processing of the polymers. As aforesaid the polymer and the probe (p-nitroaniline) were mixed together and ground into fine powder. The polymer was then placed between two clean pellets of aluminum and pressed at 8 metric tons/m² at room temperature. Compression molding above glass transition temperature confers better mechanical properties to the matrices but it seems that high temperatures promote reaction between probe and anhydride links of the polymer. Hence, compression molding was carried out at room temperature for all the polymers and even if the matrices formed in this manner were more delicate, they were still suitable for the degradation and release kinetic studies.

Erosion Kinetics

Figure 3:
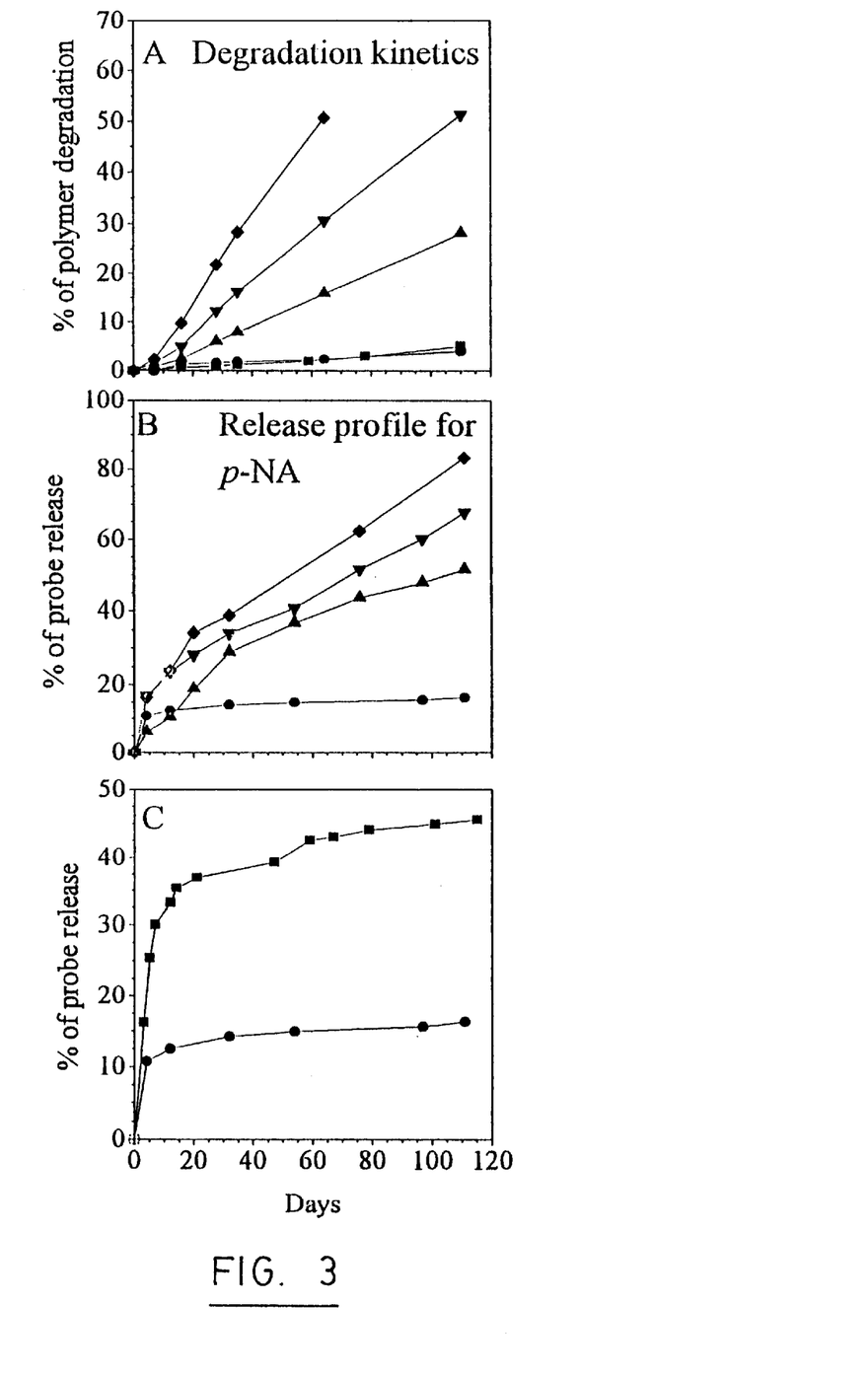
FIG. 3(A) are curves giving the degradation profiles of homo- and copolymers with a 5 wt % probe loading (PLCA●; P(LCA-co-SA) 50:50▲; P(LCA-co-SA) 20:80▼; P(LCA-co-SA) 10:90♦)
FIG. 3(B) are curves giving the release profiles of homo- and copolymers with a 5 wt % probe loading (PLCA●; P(LCA-co-SA) 50:50▲; P(LCA-co-SA) 20:80▼; P(LCA-co-SA) 10:90♦)
FIG. 3(C) are curves giving the release profiles of homopolymers of PLCA with a 20 wt % probe(●) and with; a 5 wt % probe(■)

All the polymers that were prepared and studied, have displayed constant zero-order erosion kinetics over a period of several weeks. FIG. 3 shows linear release and degradation profiles as a function of the time, for all the samples.

The decrease in the device thickness throughout the erosion, the structural integrity of the matrix and the near zero-order degradation kinetics suggest that heterogeneous surface erosion predominates. It can be estimated by extrapolation that PLCA can degrade completely in 5 years, which is much longer than ordinary degradable polymers reported in the literature.

The degradation rates were evaluated by a linear regression calculation of the degradation profile shown in FIG. 3. The degradation rates were found to be enhanced by copolymerization with sebacic acid.

As shown in Table 2, the degradation rate increased from 0.068 to 0.752 mg/d cm² as the weight proportion of sebacic acid in the polymer decreased from 90 to 0 wt %. An increase of nearly 20 times in degradation rate was observed when the sebacic acid content reaches 90 wt %.

| Weight % of SA in the polymer | Weight % of p-NA | Release rate (mg/d cm²) | Degradation rate (mg/d cm²) |
|---|---|---|---|
| 0 | 20 | 0.007 | 0.061 |
| 0 | 5 | 0.004 | 0.068 |
| 50 | 5 | 0.012 | 0.194 |
| 20 | 5 | 0.022 | 0.509 |
| 10 | 5 | 0.030 | 0.752 |

Figure 4:
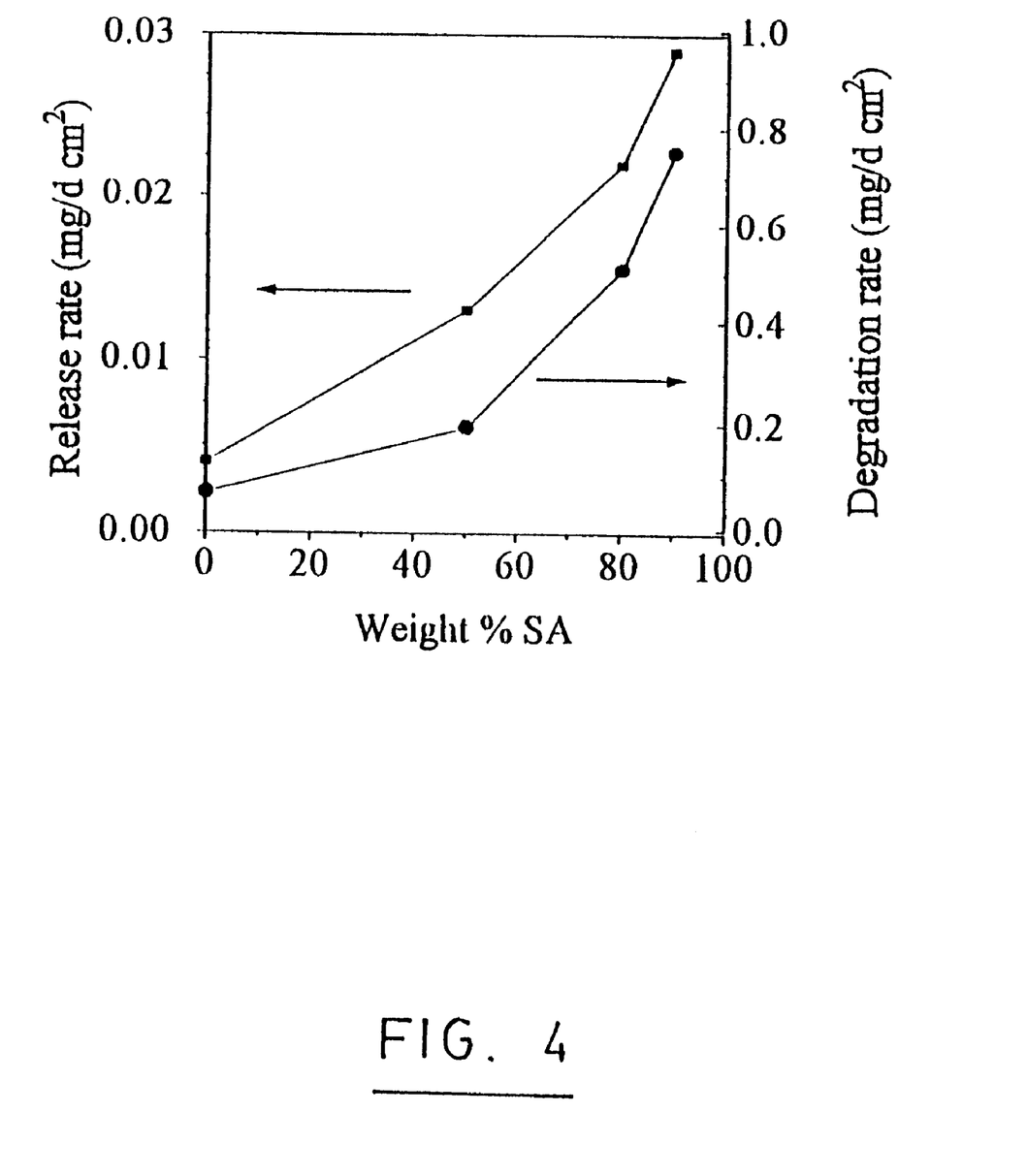
FIG. 4 is a curve showing the dependence of the release and degradation rates on the proportion of sebacic acid in the copolymers with 5 wt % probe loading (release rate of p-nitroaniline■; degradation rate of polymers●).

The dependence of the degradation rate on the sebacic acid content in the polymer is shown in FIG. 4. The more hydrophilic copolymers tend to crumble toward the later stages of degradation, around 60 wt %. The hydrolysis of anhydride links of the polymer backbone seems to control the degradation and prevent bulk degradation, since acetic acid is produced upon degradation and the polymer degrades very slowly at low pH. This is one of the intrinsic advantage of polyanhydrides, in addition to their very hydrolytically reactive linkage. Biodegradability is insured even for the highly hydrophobic homopolymer PLCA. Hence, a wide range of degradation rates can be obtained. With copolymerization, lifetime of 1 month to several years with the 150 mg pellets can be achieved. This wide range of lifetime is very important for the potential utilization of the polymers in biomedical applications.

For the release kinetic studies, p-nitroaniline was used as a probe since it is a stable compound which can mix well with the polymers. It is slightly soluble in water and absorbs strongly in UV at 455 nm. It is remarkable to observe a close correlation between the degradation and the release kinetics for the device loaded at 5 wt % of the probe. The matrices release the probe in a zero-order manner nearly parallel with the degradation profile. A zero-order profile indicates a constant release of solute with time, which is desirable because it insures a constant drug plasma level when used in controlled release systems.

Table 2 hereinabove shows the release rates and the degradation rates of the homopolymer and all the copolymers. Release rates of the probe by the polymers have been calculated by a linear regression calculation of the linear portion of the release profile in FIG. 3. The later linear portion of the release profile was used for the linear regression, and the $R^2$ value was at least 0.968 for all the analysis. Table 2 shows that the release rates increased from 0.004 to 0.030 mg/d cm² as the weight content of sebacic acid in the polymers decreased from 90 to 0 wt %.

Dependence of the release rate with sebacic acid content in the polymer is not linear, as shown in FIG. 4, but seems to follow the same trend as the degradation rate as a function of the sebacic acid content. The device loaded with 20 wt % of p-nitroaniline displays a much more rapid release of the probe during the first stage and then a zero-order release kinetic, nearly parallel with the degradation rate. The degradation rate was not as much affected by the loading percentage. For the more hydrophilic polymers, the crumbling of the device does not seem to affect the release rate of the probe. There is no sudden burst during the crumbling, usually shown by a visible inflection in the release profile.

CONCLUSION

The above reported results clearly show that the new degradable polyanhydrides according to the invention are interesting and useful as controlled release systems, since they have a very long lifetime and a degradation and release of nearly zero-order kinetic profile. These polymers also have the advantage of containing a natural compound, viz. lithocholic acid, which may enhance the biocompatibility of the new polymers.

Thus, these polymers can be used as a matrix in tablets or any other formulation (nanoparticles, . . . ) for the release of any kind of active principles in solid form at a constant rate for very long period of time, avoiding the saw-tooth patterns of conventional systemic administration. The so obtained matrices will have a predictable release rate, closely related to the degradation rate, of the polymer.

As was ecidenced hereinabove, different release rates can be obtained by adjusting the comonomer contents during the copolymerization of the lithocholic dimer with sebacic acid.

We claim:

1. A biodegradable polyanhydride, which is prepared by:
   either homopolymerization of bile acid dimers of the general formula I:

A—B—A    (I)

wherein A is a bile acid radical and B is a linear dicarboxylic acid spacer of the formula II:

—OOC—(CH$_2$)$_n$—COO—    (II)

wherein n is an integer that ranges from 1 to 12;
   or copolymerization of bile acid dimers of the general formula I as defined hereinabove, with linear dicarboxylic acids of the general formula II as defined hereinabove.

2. A biodegradable polyanhydride as claimed in claim 1, wherein n is an integer ranging from 6 to 8.

3. A biodegradable polyanhydride as claimed in claim 2, wherein the bile acid A is lithocholic acid and the linear dicarboxylic acid B is sebacic acid.

4. A biodegradable polyanhydride as claimed in claim 1, wherein said polyanhydride has an average molecular weight ranging from 12,000 to 18,000 g/mol.

5. A biodegradable polyanhydride as claimed in claim 2, wherein said polyanhydride has an average molecular weight ranging from 12,000 to 18,000 g/mol.

6. A biodegradable polyanhydride as claimed in claim 3, wherein said polyanhydride has an average molecular weight ranging from 12,000 to 18,000 g/mol.

7. A biodegradable polyanhydride as claimed in claim 1, wherein said polyanhydride is a homopolymer.

8. A biodegradable polyanhydride as claimed in claim 2, wherein said polyanhydride is a homopolymer.

9. A biodegradable polyanhydride as claimed in claim 3, wherein said polyanhydride is a homopolymer.

10. A biodegradable polyanhydride as claimed in claim 6, wherein said polyanhydride is a homopolymer.

11. A biodegradable polyanhydride as claimed in claim 1 wherein said polyanhydride is a copolymer.

12. A biodegradable polyanhydride as claimed in claim 2 wherein said polyanhydride is a copolymer.

13. A biodegradable polyanhydride as claimed in claim 3 wherein said polyanhydride is a copolymer.

14. A biodegradable polyanhydride as claimed in claim 6 wherein said polyanhydride is a copolymer.

15. A matrix for the manufacture of a controlled drug release system, said matrix being made of a biodegradable anhydride as claimed in claim 1.

16. A matrix for the manufacture of a controlled drug release system, said matrix being made of a biodegradable anhydride as claimed in claim 10.

17. A process for preparing a biodegradable polyanhydride as claimed in claim 1, comprising the steps of:

(a) heating a bile acid diner of the general formula $$A\text{—}B\text{—}A \tag{I}$$

wherein A is a bile acid radical and B is a linear dicarboxylic acid spacer of the formula II:

$$\text{—OOC—}(CH_2)_n\text{—COO—} \tag{II}$$

wherein n is an integer that ranges from 1 to 12; with acetic anhydride to produce the corresponding anhydride prepolymer; and (b) subjecting said anhydride prepolymer to melt polycondensation under an inert atmosphere in the presence or not of a linear dicarboxylic acid of the formula II as defined hereinabove.

18. A process as claimed in claim 17, wherein:

step (a) is carried out at a temperature of about 120° C. and is followed by a crystallization of the anhydride prepolymer; and step (b) is carried out by first heating the anhydride prepolymer with or without the linear dicarboxylic acid at a temperature of about 140° C. under an inert atmosphere in order to melt the prepolymer, and then allowing the polymerization to proceed in vacuo.

* * * * *

UNITED STATES PATENT AND TRADEMARK OFFICE
CERTIFICATE OF CORRECTION

PATENT NO. : 5,955,068
DATED : September 21, 1999
INVENTOR(S) : Sebastien GOUIN and Xiao-Xia ZHU It is certified that error appears in the above-identified patent and that said Letters Patent is hereby corrected as shown below:

Title page,

Item (56) References cited,     line 3: replace "Goiuin" by --Gouin--;
line 4: replace "Preparation" by --Preprint--;

Item (57) Abstract,     line 3: replace "dimer" by --dimers--;
line 4: add --of-- after "especially" and add a space after "by";

Figure 3A:     extra squares should be removed from the bottom of this Figure;

Column 2,     line 30: replace "are;" by --are:--;

Column 3,     line 38: replace "with;" by --with--;

Column 4,     line 7: delete "A." in front of "Macro";

lines 21 and 22: replace "bis (5(-cholan-24- oic acid 3(-yl)" by --bis (5 $\beta$ -cholan-24-oic 3$\alpha$-yl--;

line 29: replace "CH2" by --$CH_2$-- and "CH3" by --$CH_3$--;

line 30: replace "CH2" by --$CH_2$--; replace "J=6" by --J=6Hz-- and replace "CH3" by --$CH_3$--;

line 31: replace "CH3" (two occurrences) by --$CH_3$--;

line 42: replace "bis (5(-cholan-24-oic acid 3(-yl) sebacate" by --bis(5 $\beta$-cholan-24-oic acid 3$\alpha$-yl) sebacate--;

UNITED STATES PATENT AND TRADEMARK OFFICE
CERTIFICATE OF CORRECTION

PATENT NO. : 5,955,068
DATED : September 21, 1999
INVENTOR(S) : Sebastien GOUIN and Xiao-Xia ZHU It is certified that error appears in the above-identified patent and that said Letters Patent is hereby corrected as shown below:

Column 5, line 15: replace "naturals" by --materials--;

line 49: replace "1H" by --$^1$H--;

lines 55 and 56: replace "Mn" by --$M_n$--;

line 65: replace "sigmo dal" by --sigmoidal--;

Column 10, line 3: replace "diner" by --dimer--.

Signed and Sealed this

First Day of May, 2001

Attest:

NICHOLAS P. GODICI

Attesting Officer        Acting Director of the United States Patent and Trademark Office